United States Patent [19]

Ohnishi et al.

[11] Patent Number: 5,789,498
[45] Date of Patent: Aug. 4, 1998

[54] CURING CATALYST FOR USE IN EPOXY RESIN AND HEAT CURING COATING COMPOSITION CONTAINING THE SAME

[75] Inventors: Kazuhiko Ohnishi, Kanagawa-ken; Shigeo Nishiguchi, Hiratsuka, both of Japan

[73] Assignee: Kansai Paint Co., Ltd., Hyogo-Ken, Japan

[21] Appl. No.: 760,749

[22] Filed: Dec. 5, 1996

[30] Foreign Application Priority Data

Jul. 15, 1996 [JP] Japan .................................. 8-184357

[51] Int. Cl.[6] ........................... C08G 59/40; C08G 59/68
[52] U.S. Cl. ........................... 525/526; 528/94; 525/481; 525/484; 525/934
[58] Field of Search ............................. 525/526, 481, 525/484; 528/94

[56] References Cited

U.S. PATENT DOCUMENTS

| | | | |
|---|---|---|---|
| 3,677,978 | 7/1972 | Dowbenko et al. | 528/94 |
| 3,756,984 | 9/1973 | Klaren et al. | 528/94 |
| 4,066,625 | 1/1978 | Bolger | 525/526 |

FOREIGN PATENT DOCUMENTS

| | | |
|---|---|---|
| 46-28304 | 8/1971 | Japan . |
| 59-210930 | 11/1984 | Japan . |
| 2135316 | 8/1984 | United Kingdom . |

*Primary Examiner*—Frederick Krass
*Attorney, Agent, or Firm*—Fisher, Christen & Sabol

[57] ABSTRACT

A curing catalyst for use in epoxy resin, said curing catalyst being a metal salt complex of an adduct between polyepoxide and imidazoles; and a heat curing coating composition prepared by mixing the above curing catalyst with a coating composition containing an epoxy group-containing compound.

10 Claims, No Drawings

CURING CATALYST FOR USE IN EPOXY RESIN AND HEAT CURING COATING COMPOSITION CONTAINING THE SAME

BACKGROUND OF THE INVENTION (1) Field of the Invention

The present invention relates to a new curing catalyst for use in epoxy resin and a heat curing coating composition containing the curing catalyst.

(2) Description of the Background Art

Imidazoles have been used in the art as the curing agent for epoxy resin, and as a curing catalyst for a combination of epoxy resin with a curing agent such as a novolac phenol, acid anhydride, dicyandiamide or the like. The imidazoles may include 2-ethyl-4-methyl imidazole, 2-methyl imidazole, 2-phenyl imidazole and the like. The above imidazoles react with epoxy resin so quickly as to produce such problems that storage in a long period of time causes thickening and gelling, resulting in making it impossible to be used as one-pack type.

For the purpose of improving the above poor storage stability, for example, Japanese Patent Publication No.28304/71 discloses a curable epoxy resin composition containing a complex of imidazoles with a metal salt and epoxy resin. However, the metal complex shows poor compatibility with epoxy resin and causes to produce such problems that these components are separated from each other during storage and that the cured film shows poor finished appearance and poor performances. Further, Japanese Patent Application Laid-Open No.210930/84 discloses a metal salt complex of an adduct of imidazoles with monoepoxide as a curing agent for use in epoxy resin. Although the use of the above metal salt complex makes it possible to improve the above performances of the cured film to some extent, but not to be satisfactory, further improvements being demanded.

SUMMARY OF THE INVENTION

It is an object of the present invention to provide such a curing catalyst for use in epoxy resin that a heat curing coating composition containing the epoxy resin and the curing catalyst shows excellent performances in storage stability,and low temperature curing properties, and consequently to provide the above heat curing coating composition showing the above performances and capable of forming a cured film showing excellent performances in finished appearance, etc.

That is, the present invention provides a curing catalyst for use in epoxy resin, said curing catalyst being a metal salt complex of an adduct between polyepoxide and imidazoles; and a heat curing coating composition prepared by mixing the above curing catalyst with a coating composition containing an epoxy group-containing compound.

DETAILED DESCRIPTION OF THE INVENTION

A curing catalyst for use in epoxy resin in the present invention is a metal salt complex of an adduct between polyepoxide and imidazoles.

The polyepoxide has about two or more epoxy groups on an average in one molecule, and has an epoxy equivalent preferably in the range of from about 150 to 40,000, more preferably about 150 to 10,000. Use of the polyepoxide provides such an effect as to increase a function as an curing catalyst in that, for example, imidazoles are bonded with two or more epoxy groups in the polyepoxide, and in that the resulting adduct has two or more imidazoles per one molecule of the polyepoxide. Presence of epoxy groups less than two on an average in one molecule reduces compatibility with the epoxy group-containing compound in the coating composition, resulting in making poor storage stability of the coating composition, film finished appearance, film fabricating properties, film performances and the like.

The polyepoxide has an average molecular weight in the range of about 131 to 2,000, preferably about 300 to 1,000. Ones having the average molecular weight less than about 131 are difficult to obtain. On the other hand, use of ones having the average molecular weight more than about 2,000 makes handling of the epoxy group-containing compound difficult so as to be undesirable from the standpoint of preparation and from showing poor curing properties.

The polyepoxide may specifically include liquid ones and solid ones.

The liquid polyepoxide may include any liquid epoxy compounds and liquid epoxy resins known in the art. Examples of the liquid polyepoxide may include bisphenol/epichlorohydrin type epoxy compounds such as Epikotes 807, 828, 834, 1001, 5050 etc. (Trade name, marketed by Yuka Shell Epoxy Co., Ltd.); novolac type epoxy compounds such as DEN-431, DEN-438 etc. (Trade name, marketed by Dow Chemical Co., Ltd.); (poly)alkylene ether type epoxy compounds such as diglycidyl ether, (poly) ethylene glycol diglycidyl ether, (poly)propylene glycol diglycidyl ether, trimethylolpropane triglycidyl ether and the like; glycidyl ester type epoxy compounds such as dimer acid diglycidyl ester, phthalic acid diglycidyl ester, tetrahydrophthalic acid diglycidyl ester and the like; homopolymers of glycidyl (meth)acrylate, allyl glycidyl ether and the like, or copolymers of said monomer with other soft unsaturated monomers; other epoxy compounds such as triglycidyl isocyanurate, diglycidyl phenyl glycidyl ether and the like; and the like. The soft unsaturated monomer is such that its homopolymer has a glass transition temperature lower than 60° C., and may include, for example, methyl acrylate, ethyl acrylate, butyl (meth)acrylate, isobutyl (meth)acrylate, 2-ethylhexyl (meth)acrylate, lauryl methacrylate and the like.

The solid polyepoxide may include any solid epoxy compounds and epoxy resins known in the art, specifically, for example, bisphenol/epichlorohydrin type epoxy compounds such as Epikotes 1001, 1004, 1007 and 1009 (Trade name, marketed by Yuka Shell Epoxy Co., Ltd.), cresolnovolac type epoxy compounds such as EOCN-1020 (Trade name, marketed by Nippon Kayaku Co., Ltd.) and the like; copolymers of the epoxy group-containing unsaturated monomer with other rigid unsaturated monomers, and the like. The rigid unsaturated monomer is such that its homopolymer has a glass transition temperature of 60° C. or higher, and may include, for example, methyl methacrylate, t-butyl methacrylate, acrylonitrile, methacrylonitrile, styrene and the like.

Examples of the imidazoles may include alkyl imidazoles such as 2-ethyl-4-methyl imidazole, 1-methyl imidazole, 1,2-dimethyl imidazole, 2-methyl imidazole, 2-ethyl imidazole and the like; carbamylalkyl-substituted imidazoles such as 1-(2-carbamylethyl) imidazole and the like; alkalyl-substituted imidazoles such as 1-benzyl-2-methyl imidazole and the like; alkenyl-substituted imidazoles such as 1-vinyl-2-methyl imidazole and the like; allyl-substituted imidazoles such as 1-allyl-2-ethyl-4-methyl imidazole and the like; polyimidazole and the like.

The imidazoles preferably include alkyl imidazoles. Of these, 2-ethyl-4-methyl imidazole and 2-methyl imidazole are more preferred, and further 2-methyl imidazole is preferred from the standpoint of low temperature curing properties.

Preparation of the adduct between the polyepoxide and imidazoles may be carried out either by adding the polyepoxide to imidazoles, or by adding in a reverse order. The former adding method is preferred in that a side reaction of the polyepoxide is controlled and unnecessary increase of viscosity is controlled. A mixing ratio between the polyepoxide and imidazoles is such that the imidazoles are in the range of 0.8 to 2.0 moles, particularly 0.9 to 1.3 moles per one mole of epoxy group in the polyepoxide. When the imidazoles are in an amount less than 0.8 mole, the side reaction of the polyepoxide is increased and a viscosity in the system is undesirably increased. On the other hand, when more than 2.0 moles, increase of the amount of the imidazoles not to be reacted with the polyepoxide results in making undesirably poor coating composition storage stability, film appearance, film performances, and the like. The reaction between the polyepoxide and imidazoles may be controlled by measuring an epoxy number.

The polyepoxide may be or may not be dissolved in an organic solvent to be used. Preferably, the solid polyepoxide may be dissolved in an organic solvent to be used, or may be heated at a melting point or higher temperature to be used as a liquid.

Examples of the metal constituting the metal salt may include copper, nickel, cobalt, calcium, zinc, zirconium, silver, chromium, manganese, tin, iron, titanium, antimony, aluminum and the like. Use of a curing catalyst consisting of zinc as the metal is preferred from the standpoint of providing a coated film free of color change on curing.

Examples of the salt constituting the metal salt may include chloride, bromide, fluoride, sulfate, nitrate, acetate, malate, stearate, benzoate, methacrylate and the like. Of these, chloride and acetate are preferred. Particularly, use of a curing catalyst containing acetate as the salt is preferred in improving compatibility with the epoxy resin, and in improving film appearance (gloss), fabricating properties, and the like.

The metal salt complex between the above metal salt and the above adduct may be prepared by adding the metal salt to the adduct of the polyepoxide with the imidazoles. The metal salt may be used in the form of powder as it is, or may be dissolved or dispersed in an organic solvent to be used.

A mixing ratio of the metal salt to the adduct is such that the adduct is preferably in the range of one to 6 moles per one mole of the metal salt. Use of the adduct in an amount less than one mole reduces film performances in gloss, color change, water resistance and the like. On the other hand, use in an amount more than 6 moles reduces storage stability of the coating composition.

Next, the heat curing coating composition of the present invention is explained.

The coating composition of the present invention is prepared by mixing a metal salt complex of an adduct between the polyepoxide and the imidazoles as a curing catalyst with a coating composition containing an epoxy group-containing compound.

The coating composition of the present invention may suitably be used as a powder coating composition, or as a liquid coating composition.

The epoxy group-containing compound used in the coating composition of the present invention may include high-molecular weight various epoxy resins containing about 2 or more epoxy groups on an average in one molecule and known in the art, and may also include low-molecular weight epoxy compounds.

The epoxy compound may include liquid ones having a melting point lower than 60° C. and solid ones having a melting point of 60°0 C. or higher, preferably 60° to 200° C. The solid epoxy compound may be used as a base resin when the coating composition of the present invention is a powder coating composition. The liquid or solid epoxy compound may be used as a base resin when the coating composition of the present invention is a liquid, organic solvent type or aqueous coating composition.

The liquid epoxy compound may include any liquid epoxy compound known in the art, specifically may include the before-mentioned liquid polyepoxide for use in the metal salt complex of the present invention.

The solid epoxy compound may include any solid epoxy compounds known in the art, specifically may include the before-mentioned solid polyepoxide for use in the metal salt complex of the present invention.

A mixing amount of the metal salt complex in the coating composition of the present invention is in the range of about one to 40 parts by weight, preferably about one to 10 parts by weight per 100 parts by weight of the epoxy group-containing compound based on the solid content. A mixing amount less than about one part by weight reduces curing properties, resulting in reducing water resistance, corrosion resistance, weather resistance, fabricating properties etc. On the other hand, a mixing amount more than about 40 parts by weight undesirably reduces film appearance.

The heat curing coating composition of the present invention may include a heat curing powder coating composition prepared by mixing the metal salt complex with the above solid epoxy group-containing compound as the base resin for use in the powder coating composition. In addition to the above components i.e. the epoxy group-containing compound and the metal salt complex, the coating composition of the present invention may include a known crosslinking agent of the epoxy group-containing compound, for example, polycarboxylic acid, acid anhydride, phenol resin and the like.

Examples of the powder coating composition containing the crosslinking agent may include an epoxy-polyester hybrid type powder coating composition prepared by mixing a high-acid value polyester resin having an acid value of 100 to 500 and a softening point of 40° to 100° C. with the above bisphenol-epichlorohydrin type and/or novolac type epoxy compound at a mixing weight ratio between the epoxy group-containing compound and the high acid value polyester resin of 20/80 to 80/20; an epoxy-phenol powder coating composition prepared by mixing a phenol resin having a softening point of 40° to 100° C. with the bisphenol-epichlorohydrin type and/or the movolac type epoxy compound at a mixing weight ratio between the epoxy group-containing compound and the phenol resin of 95/5 to 80/20; an acid-curing acrylic powder coating composition prepared by mixing a polycarboxylic acid such as adipic acid, azelaic acid, dodecanoic diacid, polyadipic acid, polyazelaic acid or the like with a homopolymer of the glycidyl (meth)acrylate, or a copolymer thereof with other monomers at a mixing weight ratio between the epoxy group-containing compound and the polyearboxylic acid of 95/5 to 80/20, and the like. Use of the powder coating composition containing the above crosslinking agents provides such an effect as to further improve low temperature curing properties.

The heat curing coating composition of the present invention may also include an organic solvent type coating composition prepared by mixing a metal salt complex with an organic solvent solution obtained by dissolving or dispersing the solid epoxy group-containing compound and/or the liquid epoxy group-containing compound into an organic solvent. In addition to the epoxy group-containing compound and the metal salt complex, the organic solvent type composition may include a crosslinking agent such as polycarboxylic acid, acid anhydride, phenol resin and the like. Specifically, the same crosslinking agents as in the above powder coating composition may also be used in the organic solvent type coating composition. An organic solvent used in the organic solvent type coating composition may include any organic solvent capable of dissolving or dispersing the epoxy group-containing compound and essentially unreactive with epoxy group. Specific examples thereof may include aromatic series such as toluene, xylene and the like, alcohol series such as ethanol, propanol, butanol and the like, ether series such as ethyl cellosolve, butyl cellosolve and the like, ketone series such as methyl isobutyl ketone, ester series such as butyl acetate, cellosolve acetate and the like, and the like.

The coating composition containing the epoxy group-containing compound as used in the heat curing coating composition of the present invention may preferably include an epoxy-acid curing type coating composition containing, as the crosslinking agent, the high acid value polyester resin, polycarboxylic acid, etc.; and an epoxy-phenol curing type coating composition containing, as the crosslinking agent, the phenol resin.

In addition to the above components, the heat curing coating composition of the present invention, if needed, may include colorants, fillers, ultraviolet light stabilizers, ultraviolet light absorber, flowability adjustors, anticissing agents, antisagging agents, and the like.

The heat curing coating composition of the present invention may be coated onto a substrate, followed by heat curing at a temperature of about 120° C. or higher to form a coated film. Examples of the substrate may include metals such as iron, aluminum and the like, inorganic materials such as glass, plastics such as polyester, and ones prepared by subjecting the above substrates to the surface treatment, undercoating, etc.

Coating may be carried out by the known coating process, for example, in the case of the powder coating composition, a coating process such as the static powder coating, frictional charge powder coating, fluidization dip coating and the like, and in the case of the organic solvent type coating composition, a coating process such as the spray coating, brushing, roller coating, curtain flow coating and the like.

A coating film thickness may not particularly be limited, but is, in the case of the powder coating composition, in the range of about 30μm to 1 mm, preferably about 50 μm to 100 μm, and in the case of the organic solvent type coating composition, in the range of about 10 μm to 100 μm, preferably about 20μm to 50 μm.

The curing catalyst of the present invention provides such effects that since the metal salt complex of the adduct between the polyepoxide and imidazoles does not act as a reactive catalyst for the epoxy coating composition at a low temperature of around 40° C., the coating composition containing the curing catalyst in the present invention shows good storage stability, and since the metal salt complex is dissociated into the adduct and the metal salt by heating at a temperature around 120° C., and the imidazole component in the regenerated adduct promotes a reaction with epoxy group, resulting in providing the coating composition showing good low temperature curing properties, and further provides such effects that the use of polyepoxide as the modifier of the imidazoles improve the compatibility of the curing catalyst with the epoxy coating composition as well as curing properties of the coating composition of the present invention.

The present invention will be explained more in detail by the following Examples.

Preparation Example 1

(Preparation of metal salt complex A)

A polyepoxide organic solvent solution prepared by dissolving 375 g of Epikote 828 (Marketed by Yuka Shell Epoxy Co., Ltd., molecular weight 350, epoxy equivalent 180–195, trade name) into 375 g of methyl isobutyl ketone as an organic solvent, and having a solid content of 50% by weight was dropped onto 264 g (2.4 moles) of 2-ethyl-4-methyl imidazole with agitation over one hour, followed by reacting at 60° C. for 4 hours to obtain an adduct. The adduct had an epoxy value of 4.28/kg. The epoxy value was determined as follows. That is, a sample was dissolved into methyl ethyl ketone as an organic solvent, followed by adding an excess amount of cetyl trimethyl ammonium bromide so as to bond bromine in the cetyl trimethyl ammonium bromide with epoxy group and to form an amine, titrating the amine by use of a perchloric acid-acetic acid solution, and measuring an amount of the perchloric acid-acetic acid solution used in the titration to determine the epoxy value according to the following formula: Epoxy value (m e q)=[an amount (ml) of N/10 perchloric acid-acetic acid solution used in the present test—an amount (ml) of N10 perchloric acid—acetic acid solution used in the blank test, i.e. the organic solvent]×0.1×[a factor of N/10 perchloric acid-acetic acid solution/a residue (%) on heating the sample]×0.01×an amount (g) of the sample. Degree of conversion to the above adduct was 83%.

Next, 81.8 g (0.6 mole) of zinc chloride was added to 1014 g of the above adduct having a solid content of 63% by weight for reaction to obtain a metal salt complex A having a solid content of 66% by weight.

Preparation Example 2

(Preparation of metal salt complex B)

Experiments were carried out in the same manner as in Preparation Example 1 except that 2.4 moles of 2-methyl imidazole was used in place of the same moles of 2-ethyl-4-methyl imidazole to obtain a metal salt complex B having a solid content of 64% by weight. The adduct had an epoxy value of 4.95/kg.

Preparation Example 3

(Preparation of metal salt complex C)

Experiments were carried out in the same manner as in Preparation Example 1 except that 0.6 mole of zinc acetate dihydrate was used in place of the same mole of zinc chloride to obtain a metal salt complex C having a solid content of 67% by weight.

Preparation Example 4

(Preparation of metal salt complex D)

A mixture of 83 g (one mole) of 2-methyl imidazole and 150 g (one mole) of phenyl glycidyl ether in a toluene organic solvent was reacted at a reflux temperature for 2 hours, followed by removing the solvent under vacuum to obtain an epoxy-imidazole adduct. The adduct had an epoxy value of 4.31/kg. Next, 233 g (one mole) of the epoxy-imidazole adduct was dissolved in methanol, followed by adding 42.5 g (0.25 mole) of cupric chloride dihydrate for carrying out reaction to obtain a metal salt complex D having a solid content of 50% by weight.

Preparation Example 5

(Preparation of metal salt complex E)

A mixture of 83 g (one mole) of 2-methyl imidazole and 150 g (one mole) of phenyl glycidyl ether in a toluene organic solvent was reacted at a reflux temperature for 2 hours, followed by removing the solvent under vacuum to obtain an epoxy. imidazole adduct. The adduct had an epoxy value of 4.29/kg.

Next, 233 g (one mole) of the epoxy. imidazole adduct was dissolved in methanol, followed by adding 55 g (0.25 mole) of zinc acetate dihydrate for carrying out reaction to obtain a metal salt complex E having a solid content of 50% by weight.

The following Examples 1-7 and Comparative Examples 1-4 relate to an organic solvent type coating composition.

Example 1

Sixty grams of Epikote 1001 (Marketed by Yuka Shell Epoxy Co., Ltd., trade name, bisphenol A-epichlorohydrin type epoxy resin, epoxy equivalent 425-550, molecular weight 900, melting point 64°-76° C.) was dissolved in 40 g of xylol to obtain an epoxy resin solution having a solid content of 60% by weight. Next, 167 g (100 g as the solid content) of the epoxy resin solution was mixed with 7.5 g (5 g as the solid content) of the metal salt complex A to obtain an organic solvent type coating composition of Example 1.

Examples 2-7 and Comparative Examples 1-4

The organic solvent type coating compositions of Examples 2-7 and Comparative Examples 1-4 were prepared according to the formulations shown in Table 1 respectively.

TABLE 1

|  | Examples | | | | | | | Comparative Examples | | | |
|---|---|---|---|---|---|---|---|---|---|---|---|
|  | 1 | 2 | 3 | 4 | 5 | 6 | 7 | 1 | 2 | 3 | 4 |
| Epikote 1001 | 100 | 100 | 100 |  |  | 100 | 100 | 100 | 100 |  |  |
| Epiclon FK-5300 |  |  |  | 100 | 35 |  |  |  |  | 100 | 35 |
| ZX-798 |  |  |  |  | 65 |  |  |  |  |  | 65 |
| Metal salt complex |  |  |  |  |  |  |  |  |  |  |  |
| Kind | A | B | C | A | A | A | A | D | E | D | D |
| amount | 5 | 5 | 5 | 5 | 5 | 1 | 10 | 5 | 5 | 5 | 5 |
| Resin solid content (xylol) |  |  |  |  | 50% by weight | | | | | | |

In Table 1, Epiclon FK-5300 represents a trade name of a movolac epoxy resin having an epoxy equivalent of 370 and a solid content of 70% by weight and marketed by Dainippon Ink & Chemicals Inc., and ZX-798 represents a trade name of a phenol resin solution prepared by dissolving a phenol resin having a phenol equivalent of 700 into xylene, and having a solid content of 60% by weight and marketed by Tohto Kasei Co., Ltd.

Coating composition properties and film performance test results obtained according to the following test methods by use of coating compositions of Examples 1-7 and Comparative Examples 1-4 are shown in the following Table 2.

TABLE 2

|  | Examples | | | | | | | Comparative Examples | | | |
|---|---|---|---|---|---|---|---|---|---|---|---|
|  | 1 | 2 | 3 | 4 | 5 | 6 | 7 | 1 | 2 | 3 | 4 |
| Initial film performances |  |  |  |  |  |  |  |  |  |  |  |
| specular reflection percentage | 92 | 92 | 95 | 92 | 94 | 95 | 90 | 78 | 80 | 76 | 77 |
| film appearance | 3 | 3 | 3 | 3 | 3 | 3 | 3 | 3 | 3 | 3 | 3 |
| film color change | 3 | 3 | 3 | 3 | 3 | 3 | 3 | 1 | 3 | 1 | 1 |
| curing properties | 3 | 3 | 3 | 3 | 3 | 3 | 3 | 3 | 3 | 3 | 3 |
| flexing properties | 4 | 4 | 4 | 4 | 4 | 3 | 4 | 3 | 2 | 3 | 3 |
| impact resistance | 4 | 4 | 4 | 4 | 4 | 3 | 4 | 3 | 2 | 3 | 3 |
| Coating Composition storage stability | 3 | 3 | 3 | 3 | 3 | 3 | 3 | 2 | 1 | 2 | 2 |
| Film performances after storage |  |  |  |  |  |  |  |  |  |  |  |
| specular reflection percentage | 90 | 91 | 92 | 90 | 90 | 95 | 88 | 60 | 52 | 58 | 51 |
| film appearance | 3 | 3 | 3 | 3 | 3 | 3 | 3 | 2 | 2 | 2 | 2 |
| curing properties | 3 | 3 | 3 | 3 | 3 | 3 | 3 | peeled film | | | |
| flexing properties | 4 | 4 | 4 | 4 | 4 | 3 | 3 | 2 | 2 | 2 | 2 |
| impact resistance | 4 | 4 | 4 | 4 | 4 | 3 | 3 | 2 | 2 | 2 | 2 |

Coating composition properties and film performance tests shown in Table 2 were carried out as follows.

Initial Film Performance Tests

Preparation of coated test panels:

Coating compositions of Examples 1-7 and Comparative Examples 1-4 were coated to be a dry film thickness of about 40 μm onto a zinc phosphate-treated steel sheet by spay coating, followed by heat curing at 130° C. for 20 minutes to obtain coated test panels respectively.

Specular reflection percentage:

Degree of gloss of the film is represented according to the 60° specular gloss defined in JIS K5400.

Film appearance:

A coated surface was examined by the naked eye to evaluate as follows. 3: Nothing abnormal is observed in smoothness, shrinkage, etc. 2: Some abnormalities are observed in smoothness, shrinkage, etc. 1: Remarkable abnormalities are observed in smoothness, shrinkage, etc.
Film color change:

Color change based on comparison between a color of a film prior to curing and that of a film after curing was examined by the naked eye to evaluate as follows.

3: No color change is observed to be good. 2: Some color change is observed. 1: Remarkable color change is observed.
Curing properties:

A coated surface was wiped reciprocally 50 times with a gauge impregnated with methyl ethyl ketone strongly pressing with fingers to evaluate film appearance by the naked eye. 3: The coated surface shows nothing abnormal and shows good curing properties. 2: The coated surface shows a little marks and shows poor curing properties. 1: The coated surface is dissolved and shows very poor curing properties.
Flexing properties:

A test was carried out by use of a flexing resistance tester, a shaft of which has a diameter of 10 mm, according to JIS K-5700. 4: None of cracking and peeling was observed. 3: Development of small crazes is observed, but no peeling is observed to be good. 2: Development of both cracking and peeling is observed. 1: Remarkable development of both cracking and peeling is observed.

Impact Resistance:

Impact was given onto the coated surface of a coated sheet under the conditions of a falling weight of 500 g, a diameter of a pointed end of a shock mold of ½ inch and a falling height of 50 cm in accordance with Dupont impact tester to observe development of cracking and peeling of the coated film. 4: Neither cracking nor peeling is observed. 3: Small crazes are observed, but peeling is not observed to be good. 2: Development of both cracking and peeling is observed. 1: Remarkable development of both cracking and peeling is observed.
Coating composition storage stability:

A coating composition is diluted so as to have a viscosity of about 2 poise and to be used as a sample. The sample was stored at 40° C. for 3 days under a closed condition, followed by measuring a viscosity of the sample to evaluate as follows. 3: Increase of the viscosity is in the range of 0 to 10 poise. 2: Increase of the viscosity is in the range of 11 to 100 poise. 1: Gelation is observed.

Film Performance Tests after Storage

Film performance tests were carried out in the same manner as in the above initial film performance tests by use of a coating composition which has been subjected to the above storage stability test.

Examples 8–16 and Comparative Examples 5–10 relate to a powder coating composition.

Example 8

A mixture of 1000 g of Epikote 1004 (Marketed by Yuka Shell Epoxy Co., Ltd., trade name, bisphenol A-epichlorohydrin type epoxy resin, epoxy equivalent 875–1025, molecular weight 1400, melting point 90°–103° C.) with 50 g (as the solid content) of the metal salt complex A was subjected to dry dispersion and mixing in a Henschel mixer, followed by subjecting to a biaxial melt mixing and dispersion, cooling, granulating, finely grinding, and filtering through 150 mesh to obtain a powder coating composition of Example 8.

Examples 9–16 and Comparative Examples 5–10

The powder coating compositions of Examples 9–16 and Comparative Examples 5–10 were prepared according to the formulations shown in Table 3 respectively.

TABLE 3

| | Examples | | | | | | | | | Comparative Examples | | | | | |
|---|---|---|---|---|---|---|---|---|---|---|---|---|---|---|---|
| | 8 | 9 | 10 | 11 | 12 | 13 | 14 | 15 | 16 | 5 | 6 | 7 | 8 | 9 | 10 |
| Epikote 1004 | 100 | 100 | 100 | | | 40 | | 100 | 100 | 100 | 100 | | | 40 | |
| Epiclon FK-5800 | | | | 100 | 53 | | | | | | | 100 | 53 | | |
| ZX-798 | | | | | 47 | | | | | | | | 47 | | |
| U-PICA COAT GV-340 | | | | | | 60 | | | | | | | | 60 | |
| Acrylic resin | | | | | | | 80 | | | | | | | | 80 |
| Dodecanoic diacid | | | | | | | 20 | | | | | | | | 20 |
| Metal salt complex | | | | | | | | | | | | | | | |
| kind | A | B | C | A | A | A | A | A | A | D | E | D | D | D | D |
| amount | 5 | 5 | 5 | 5 | 5 | 5 | 5 | 1 | 10 | 5 | 5 | 5 | 5 | 5 | 5 |

In table 3, Epiclon 5800 represents a trade name of a novolac epoxy resin having an epoxy equivalent of 750–850 and a melting point of 96°–100° C. and marketed by Dainippon Ink & Chemicals Inc., and U-PICA COAT GV-340 represents a trade name of a high acid value polyester resin having a melting point of 126° C. and an acid value of 32, and marketed by Japan U-PICA Co., Ltd.

Coating composition properties and film performance test results obtained according to the following test methods by use of coating compositions of Examples 8–16 and Comparative Examples 5–10 are shown in the following Table 4.

TABLE 4

|  | Examples ||||||||| Comparative Examples ||||||
|---|---|---|---|---|---|---|---|---|---|---|---|---|---|---|---|
|  | 8 | 9 | 10 | 11 | 12 | 13 | 14 | 15 | 16 | 5 | 6 | 7 | 8 | 9 | 10 |
| Initial film performances |
| specular reflection percentage | 90 | 90 | 92 | 88 | 92 | 93 | 95 | 93 | 88 | 81 | 80 | 79 | 78 | 80 | 81 |
| film appearance | 3 | 3 | 3 | 3 | 3 | 3 | 3 | 3 | 3 | 3 | 3 | 3 | 3 | 3 | 3 |
| film color change | 3 | 3 | 3 | 3 | 3 | 3 | 3 | 3 | 3 | 1 | 3 | 1 | 1 | 1 | 1 |
| curing properties | 3 | 3 | 3 | 3 | 3 | 3 | 3 | 3 | 3 | 3 | 3 | 3 | 3 | 3 | 3 |
| flexing properties | 4 | 4 | 4 | 4 | 4 | 4 | 4 | 3 | 4 | 3 | 3 | 3 | 3 | 3 | 3 |
| impact resistance | 4 | 4 | 4 | 4 | 4 | 4 | 4 | 3 | 4 | 3 | 3 | 3 | 3 | 3 | 3 |
| Film performances after storage |
| specular reflection percentage | 86 | 88 | 90 | 86 | 91 | 90 | 92 | 91 | 85 | 50 | 46 | 51 | 50 | 52 | 50 |
| film appearance | 3 | 3 | 3 | 3 | 3 | 3 | 3 | 3 | 3 | 2 | 2 | 2 | 2 | 2 | 2 |
| curing properties | 3 | 3 | 3 | 3 | 3 | 3 | 3 | 3 | 3 |  |  | peeled film |||
| flexing properties | 4 | 4 | 4 | 4 | 4 | 4 | 4 | 3 | 4 | 2 | 2 | 2 | 2 | 2 | 1 |
| impact resistance | 4 | 4 | 4 | 4 | 4 | 4 | 4 | 3 | 4 | 2 | 2 | 2 | 2 | 2 | 2 |

In Table 4, the coating composition properties and film performance tests were carried out as follows.

Initial film performance tests

Preparation of coated test panels:

Coating compositions of Examples 8–16 and Comparative Examples 5–10 were coated to be a dry film thickness of about 80 μm onto a zinc phosphate-treated steel sheet by an electrostatic powder coating, followed by heat curing at 140° C. for 30 minutes to be used as a coated test panel respectively.

Tests of specular reflection percentage, film appearance, curing properties, flexing properties and impact resistance were carried out in the same manner as in the above organic solvent type coating composition.

Film color change:

Tests were carried out in the same manner as in the above organic solvent type coating composition except that a coated film prior to heat curing was heat cured at 140° C. for 5 minutes or shorter so that the coated film may be in an uncured state to be tested.

Film performance tests after storage:

The powder coating compositions of Examples 8–16 and Comparative Examples 5–10 were stored at 40° C. for 3 days, followed by carrying out the same film performance tests as in the organic solvent type coating composition.

What is claimed is:

1. A curing catalyst for use with an epoxy resin, said curing catalyst being a divalent metal salt complex of an adduct between a polyepoxide and an imidazole, said adduct being the reaction product of (1) a glycidyl ether of a polyphenol having an epoxy equivalent of 150 to 10,000 and (2) an imidazole, said adduct being the reaction product of 0.9 to 1.3 moles (2) per mole of epoxy group in (1), wherein the metal salt complex is the reaction product of 1 to 6 moles of said adduct per mole of a divalent metal salt.

2. A catalyst as claimed in claim 1, wherein the metal salt is a zinc salt.

3. A catalyst as claimed in claim 1, wherein the metal salt is at least one metal salt selected from the group consisting of zinc chloride and zinc acetate.

4. A catalyst as claimed in claim 1, wherein the metal salt is zinc acetate.

5. A heat curing coating composition prepared by mixing a divalent metal salt complex of an adduct between polyepoxide and imidazole as a curing catalyst with a coating composition containing an epoxy group-containing compound, said adduct being the reaction product of (1) a glycidyl ether of a polyphenol having an epoxy equivalent of 150 to 10,000 and (2) an imidazole, said adduct being the reaction product of 0.9 to 1.3 moles (2) per mole of epoxy group in (1), wherein the metal salt complex is the reaction product of 1 to 6 moles of said adduct per mole of a divalent metal salt, wherein the metal salt complex is mixed in an amount of one to 40 parts by weight per 100 parts by weight of the epoxy group-containing compound as a solid content.

6. A coating composition as claimed in claim 5, wherein the metal salt complex is mixed in an amount of one to 1 parts by weight per 100 parts by weight of the epoxy group-containing compound as a solid content.

7. A coating composition as claimed in claim 5, wherein the coating composition containing the epoxy group-containing compound is an epoxy-phenol curing coating composition.

8. A coating composition as claimed in claim 5, wherein the coating composition containing the epoxy group-containing compound is an epoxy-acid curing coating composition.

9. A coating composition as claimed in claim 5, wherein said heat curing coating composition is a heat curing powder coating composition.

10. A coating composition as claimed in claim 5, wherein said heat curing coating composition is an heat curing organic solvent coating composition.

* * * * *